United States Patent [19]

Gassel

[11] 4,065,561

[45] Dec. 27, 1977

[54] METHOD OF INDUCING SKELETAL MUSCLE RELAXATION

[76] Inventor: Myron Michael Gassel, 34555 Scenic Drive, Dana Point, Calif. 92629

[21] Appl. No.: 592,124

[22] Filed: June 30, 1975

[51] Int. Cl.$^2$ ............................................. A61K 31/44
[52] U.S. Cl. .................................................... 424/263
[58] Field of Search ............................... 424/274, 203

[56] References Cited

PUBLICATIONS

Yamamoto, I. et al., Nara Igaku Zasshi 9:36–47, (1958).
Larson, P. S. et al., Arch. Int. Pharmacodynamie, 83, 191–192, (1950).
Dingemanse et al., Arch. Exp. Path Pharmakol., 132365–381, (1928).
Oosterhuis et al., J. P. Rec. Trev. Chim. 55:729–736, (1936).
Kitamura, T., Fol. Pharm. Japan, (Brevearia), 54:825–837, (1958).
Clark et al. Arch Int. Pharmcodyne, 156:343–379, (1965).
Audier; A. G., Antonie Var Lecuivenhoch, 17:29–57, (1951).

*Primary Examiner*—Stanley J. Friedman

[57] ABSTRACT

This invention relates to a method for inducing skeletal muscle relaxation in mammals suffering from pathological states that are characterized by hyperactivity of the spinal reflex arc, such as, for example, painful muscle spasm or spasticity, which comprises the administration to such a mammal of a non-toxic pharmaceutically effective amount of 1-methyl-2-(3-pyridyl) pyrrole or 1,5-dimethyl-2-(3-pyridyl) pyrrole.

6 Claims, No Drawings

METHOD OF INDUCING SKELETAL MUSCLE RELAXATION

This invention relates to a method of effecting skeletal muscle relaxation in mammals suffering from pathological states that are characterized by hyperactivity of the spinal reflex arc.

The invention sought to be patented resides in the concept of inducing skeletal muscle relaxation by directly and specifically reducing hyperactivity in the nervous centers concerned with the stretch reflex, as in spasticity; and with the flexion reflex, as in painful muscle spasm or the hyperactive withdrawal reflex. Nontoxic pharmacologically active amounts of 1-methyl-2-(3-pyridyl)-pyrrole and 1,5-dimethyl-2-(3-pyridyl) pyrrole, and the acid-addition and quaternary ammonium salts thereof, depress spinal stretch and flexion reflexes and impair the recovery of spinal reflex excitability, with a high level of specificity.

The 1-methyl-2-(3-pyridyl) pyrrole used in the practice of this invention is a known compound that is conveniently prepared, as described by Wibaut, J. P. and Overhoff, J., Jrn. of Rec. Trav. Chim., 47:935 (1928), by the catalytic dehydrogenation of nicotine. The 1,5-dimethyl-2-(3-pyridyl) pyrrole is conveniently prepared by treating $\beta$-nicotyrine with phosphorus oxychloride in the presence of dimethylformamide to form 1-methyl-5-(3-pyridyl)-pyrrole-2-carboxaldehyde which is subjected to a Wolff-Kishner reduction to yield the the desired 1,5-dimethyl-2-(3-pyridyl) pyrrole.

The category of centrally acting skeletal muscle relaxants, to which reference is made in this specification, is that produced by drugs acting on the central nervous system by depressing the excitability or responsiveness of spinal motor-neurones and skeletal muscle reflexes. It is to be differentiated from neuromuscular blocking agents, such as curare, which produce skeletal muscle relaxation by a peripheral action, blocking the neuromuscular junction.

Hyperactivity of the stretch reflex is associated with the clinical state of spasticity with clonus. Hyperactivity of the flexion reflex is an established component of spasticity, and the spasm associated with this hyperactivity is an important clinical therapeutic problem. The flexion reflex is also engaged in the muscle spasm associated with the painful low back pain and, indeed, with the painful muscle spasm of almost any etiology.

The centrally acting variety of muscle relaxant drug is prescribed in pathological conditions with exaggeration of stretch or flexion reflexes. It produces a therapeutic effect by depressing the hyperactivity without affecting voluntary use of the muscles. Neuromuscular blocking agents, acting peripherally, produce skeletal muscle flaccidity and paralysis affecting both voluntary and reflex activation globally.

The centrally acting muscle relaxants currently in use produce a significant level of sedation. (D. W. Esplin, Chapt. 14, The Pharmacological Basis of Therapeutics, ed. Goodman and Gillman, 4th ed., London, MacMillan, (1970). On the other hand, sedatives induce some degree of central muscle relaxation. Diazepam and pentobarbital, for example, have been shown to produce a similar pattern of global depression, with concomitant sedation and reflex inhibition. (M. M. Gassel, New Developments in Electromyography and Clinical Neurophysiology, ed. by Desmedt, Vol. 3:342-359, Karger, Basel (1973). Indeed, the specificity of action of central muscle relaxants in humans as distinct from that of sedatives or tranquilizers is problematical.

A basic factor limiting the evaluation of therapeutic effectiveness of muscle relaxants in humans has been the lack of objective criteria for analyzing drug action. Clinical judgment alone has proved to be inadequate in evaluating drug effect; patients' subjective reports of change are frequently inaccurate, and objective techniques currently employed, such as electromyography, are invalid. Clinical study of drug action is also generally overly circumscribed without evaluation of the frequently significant contribution of sedation or analgesia to overall effectiveness. On the other hand, neuropharmacological techniques for predicting clinical effectiveness based on animal experiments have been found wanting. The neurophysiological criteria for establishing activity as a "muscle relaxant" lack established clinical validity. Animal models reproducing clinical disorders have been difficult to construct and have provided only a modest basis for predicting clinical pharmacology.

An objective technique has been described employing the methodology of clinical neurophysiology, for providing evidence of therapeutic effectiveness of muscle relaxants in humans. (Gassel, M. M., New Developments in Electromyography and Clinical Neurophysiology, ed. by Desmedt, Vol. 3:342-359, Karger, Basel (1973). This comprises a comprehensive evaluation of drug effects using objective criteria in a controlled setting. Stretch reflexes, evaluated in the same population of triceps surae motoneurones, are the mechanically evoked reflex (ankle jerk) and the electrically evoked reflex (technique of paired stimuli). The activity of the flexion reflex afferent system is studied in normal subjects by changes in excitability evoked in the same group of triceps surae motoneurones on stimulating cutaneous afferents employing a new technique. The activity of the flexion reflex is also evaluated in patients with spasticity by changes in ipsilateral or crossed effects evoked by an invariable shock stimulus delivered to the skin of the distal foot.

Aggravation of spasticity and clonus has been demonstrated in patients with spasticity during periods with objective evidence of facilitation of reflex excitability and recovery produced by a drug, and improvement of clinical status with decrease in spasticity and the flexion reflex in association with depression of reflex excitability and recovery. The depression of reflex recovery at the height of intercurrent facilitation is a particularly sensitive and useful criterion of effective action as a muscle relaxant.

The characteristics and significance of the recovery cycle of the monosynaptic reflex in disease states has recently been reviewed. (Gassel, M. M., J. Neurol. Neurosurg. Psychiat., 33:358-362 (1970). A stimulus which evokes a maximal reflex is followed at intervals by an identical stimulus. The plot of the amplitude of the conditioned reflex relative to that of the unconditioned reflex as a function of the time interval between the reflexes, represents the temporal pattern of recovery of excitability after a reflex. A phase of "intercurrent facilitation" occurring from 50 to 400 msec and peaking at about 200 msec is the most sensitive parameter of disease states. It is enhanced and occurs with shorter latency in patients with spasticity; it is heightened in Parkinson's disease and depressed after successful thalamotomy; it is abolished during spinal shock in humans and then increases with return of muscle tone, finally becoming enhanced with the development of spasticity. Changes in reflex recovery at the height of intercurrent facilitation are also a sensitive criterion of drug action and it is especially noteworthy that it is possible to predict the clinical utility of a centrally acting muscle relaxant drug from preliminary analysis of action in normal subjects. In clinical studies reflex alterations are related to changes in psyche evaluated subjectively and by a test of intellectual performance, and to clinical effects evaluated at regular intervals. A comparison is made with the effects of doses of barbiturates and diazepam to judge further the relationship of sedation to the observed changes.

These criteria have been adapted to animal studies, and it is on this evidence, supplemented by classical criteria, that the method comprising the present invention is based.

The 1-methyl-2-(3-pyridyl) pyrrole and 1,5-dimethyl-2-(3-pyridyl) pyrrole compounds that are used in the practice of this invention each contain a five-membered heterocyclic ring system that is linked to pyridine as is found in the tobacco alkaloid nicotine. These compounds are represented by the following structural formulae:

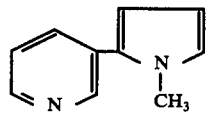
1-methyl-2-(3-pyridyl) pyrrole

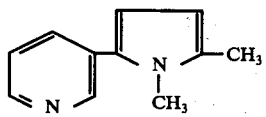
1,5-dimethyl-2-(3-pyridyl) pyrrole

It is noteworthy that neither of the compounds represented by this formula possess a nitrogen atom which will be protonated at physiological pH, a priori evidence against any significant nicotinic or muscarinic activity.

There have been decided discrepancies in reports of physiological properties of 1-methyl-2-3-pyridyl-pyrrole. It has been stated variously to produce in the dog, no change in blood pressure (Yamamoto, I., et al, Nara Igaki Zasshi., 9:36-47, (1958), or an elevation of blood pressure varying in reports from 1/50th to 1/100th that produced by nicotine (Larson, P. S., et al, Arch. Int. Pharmacodyn, 83, 191-192, (1950); whereas, in the cat there have been reports of hypotension (Dingemanse, E. and Wibaut, J. P., Arch. Exp. Path. Pharmakol, 132, 365-381 (1928); Oosterhuis, A. G. and Wibaut, J. P., Rec. Trav. Chem., 55:729-736 (1936), and hypertension of 1/50th to 1/100th that of nicotine (Larson, P. S., et al, Arch. Int. Pharmacodyn, 82:191-192 (1950). The compound has otherwise been found to produce no remarkable effect on the autonomic nervous system even at high doses (Kitamura, T. Fol. Pharm., Japan, (Breviaria) 54:825-837, (1958). 1-methyl-2-3-pyridyl-pyrrole produced depression of the monosynaptic reflex of 1/6th the potency of nicotine, and inhibition of the flexion reflex 1/10th that of nicotine in the cat; while in the spinal chick the inhibition of the flexion reflex was ½ as effective of nicotine and depression of crossed extension 1/10th that of nicotine (Clark, M. S. G., et al, Arch. Int. Pharmacodyn, 156:343-379 (1965).

1-methyl-2-3-pyridylpyrrole was experimentally employed in man (Audier, A. G., Antonie Van Leeuwenhoek, 17:29-57 (1951) as a local bacteriostatic and antipyorrheic agent applied as a 4% ointment, a dose estimated to be equivalent to 1 mgm. per kg. administered parenterally. Audier observed that the chemical, injected subcutaneously into mice at a dose equal to 150 mgm./kg. together with nicotinic acid, caused the animals to lie quietly on their sides although without affecting their ability to walk. They appeared to be easily tired by walking. The nicotinic acid injected alone was without effect on the animals. At the present time there is no known clinical application for 1-methyl-2-(3-pyridyl) pyrrole or 1,5-dimethyl-2-(3-pyridyl) pyrrole.

The present invention relates to a novel therapeutic application, as a centrally acting mammalian skeletal muscle relaxant, of 1-methyl-2-(3-pyridyl) pyrrole and its 1,5-dimethyl-2-(3-pyridyl) pyrrole derivative. Both of these drugs inhibit spinal reflex excitability and recovery with little effect on blood pressure, pulse or respiration. The depression of reflex recovery is predominant. This depression has been defined as the most sensitive and reliable index of effectiveness as a central muscle relaxant. No change in behavior of the intact animal is observed at doses five to ten times that demonstrated to depress spinal reflex activity and diminish spasticity and the flexion reflex in the animal preparation. The drug is well and rapidly absorbed orally, and there is a wide range between effective dose and the $LD_{50}$. At high doses mice and rats show an ascending hind-limb paresis, muscle flaccidity, retardation of spontaneous movement and loss of the righting and flexion reflexes. All observable effects are reversed in surviving animals.

For use in the practice of this invention, the 1-methyl-2-(3-pyridyl) pyrrole and 1,5-dimethyl-2-(3-pyridyl) pyrrole can, if desired, be converted into their non-toxic pharmaceutically acceptable acid-addition or quaternary ammonium salts. Salts which may be formed comprise, for example, salts with inorganic acids, such as the hydrochloride, hydrobromide, hydroiodide, sulfate, phosphate or the like. They may also comprise salts with organic acids, including monobasic proprionate, and especially those with hydroxy organic acids and dibasic acids, such as citrate, tartrate, malate and maleate. Pharmaceutically, the salt will not be substantially more toxic than the free base from which it is prepared and, to be acceptable, it should be able to be incorporated into conventional liquid or solid pharmaceutical media. Among such useful quaternary ammonium salts are those formed with such alkyl halides as methyliodide, n-hexylbromide and the like. The use of such pharmaceutically acceptable acid-addition or quaternary ammonium salts in the practice of this invention is fully equivalent to the use of the free bases from which they are derived, and such use is included within the scope of this invention.

In carrying out the method according to this invention, the active ingredient is normally combined with conventional pharmaceutical diluents and carriers which are selected based upon the desired route of administration. The oral route is preferred due to ease of administration.

The individual unit dose and frequency of administration is determined not only by the nature and severity of the subject's condition for which muscle relaxation is desired, but in addition upon the age, weight and species of the subject, the underlying physical condition and the route of administration. It will, accordingly, be within the professional judgment and skill of the practitioner administering the drug to determine the exact amount to be administered such as to be non-toxic, yet sufficient to induce a state of muscle relaxation in the subject.

The best mode contemplated by the inventor for carrying out this invention will now be set forth as follows:

The technique of preparation and purification of 1-methyl-2-(3-pyridyl) pyrrole is modified and adapted from that described by Wibaut, J. P. and Overhoff, J., J. Rev. Trav. Chim., 47: 935-9 (1928). In this method naturally occurring nicotine is submitted to high temperature catalytic (palladium over carbon) dehydrogenation over a 12 hour period maintaining a slow nitrogen sweep. Purification of the product is achieved through fractional distillation employing a spinning band column in order to remove minute amounts of residual nitrogen.

EXAMPLE 1

1-Methyl-2-(3-pyridyl) pyrrole

Nicotine (freshly vacuum distilled at 15 mm. Hg 110° C is dissolved in an equal volume of redistilled p-cymene. To this mixture is added 1 g/100 g nicotine of 10% palladium on carbon. With vigorous stirring under nitrogen the mixture is heated to reflux—the nitrogen is used to sweep the system to remove hydrogen generated. Periodic (every 6 hours) gas liquid partition chromatography (glpc) analyses (150°, OV17-column 6 foot by ⅛ inch) are run to follow the reaction. After 54 hours the reaction mixture consists of nicotine:1-methyl-2-(3-pyridyl) pyrrole: unknown compound in a ratio of 1:50:1. After removing the p-cymene in vacuo, vacuum distillation (adiabatic annular teflon spinning band distillation column) at 5mm gives two fractions. Fraction 1 (boiling point 122°-129° C) consists of a mixture of nicotine and 1-methyl-2-(3-pyridyl) pyrrole (by glpc 1:3) Fraction II (boiling point 129°-130° is pure 1-methyl-2-(3-pyridyl) pyrrole (by glpc and nuclear magnetic resonance). The yield of pure beta-nicotyrine is about 40% although redistillation of Fraction I will improve the overall yield significantly.

The 1,5-dimethyl-2-(3-pyridyl) pyrrole is prepared from 1-methyl-2-(3-pyridyl) pyrrole by treatment with phosphorus oxychloride and dimethyl formamide to form a pyrrole-carboxaldehyde which is then subjected to a Wolff-Kishner reduction.

EXAMPLE 2 a. 1-Methyl-5-3-pyridyl) pyrrole-2-carboxaldehyde

To a solution of freshly distilled dimethylformamide (50g) containing freshly distilled phosphorous oxychloride (15 g, 10 mmoles is added dropwise 1-methyl-2-(3-pyridyl) pyrrole (8 L g, 10 mmoles). The mixture is stirred an additional 2 hr at room temperature and then added to sodium acetate (19 g, 100 mmoles) in 100 ml ice water. The pH of the resulting mixture is adjusted to 12 with 1 N. sodium hydroxide and the basic solution exhaustively extracted with methylene chloride (4 × 50 ml). The combined organic layers are back extracted with dilute phosphoric acid (3 × 25 ml) and the aqueous layer washed once with methylene chloride (50 ml) and once with hexane. The pH of the aqueous layer is adjusted to 10 with 1 N. sodium hydroxide and the mixture extracted with methylene chloride (3 × 50 ml). The combined, dried (magnesium sulfate) organic layers are concentrated to yield 8 g (4.3 mmoles, 86%) crude product. Crystallization from petroleum ether (30°-60° C) yields the pure compound: mp 56°-56.5° C (lit. mp 56°-56.5° C): NMR (CDCL$_3$) 8 9.80 ppm (s, CHO)c 8.84, 7.92, 7.54 (pyridine aromatic signals), 7.15 and 6.49 (d, J=5, pyrrole aromatic signals), 4.22 (s, CH$_3$).

b. 1,5-Dimethyl-2-(3-pyridyl) pyrrole

A mixture of 1-methyl-5-(3-pyridyl) pyrrole-2-carboxaldehyde (8.0 g, 43 mmoles), hydrazine hydrate (8.0 g, 160 mmoles) and potassium hydroxide (10.6 g of 85% pellets) in 80 ml triethyleneglycol is stirred at 125° L C for 75 min. during which time vigorous evolution of gas is observed. The temperature is then increased to 175° C and stirring continued until evolution of gas ceases. After cooling, the reaction mixture is extracted with 3 × 50 ml portions of diethyl ether. The combined ether layers are dried (anhydrous magnesium sulfate) and removed under vacuum. Fractional vacuum distillation of the residue provides the pure product.

NMR (CDCl$_3$): 2.2ppm (CCH$_3$), 3.4 (NCH$_3$), 5.9 and 6.2 (pyrrole aromatic signals), 7.3, 7.6, 8.6, and 9.1 (pyridine aromatic signals).

EXAMPLE 3

Acute toxicity determinations were made in accordance with standard test procedures. A gross post mortem examination was made in animals which received lethal doses. Surviving animals were observed 10 days and then sacrificed for post mortem. No abnormality was found.

LD$_{50}$: mice, oral route; 575 mgm./kg. mice, I.P.; 325 mgm./kg. rats, I.V.; 750 mgm./kg.

1-methyl-2-(3-pyridyl) pyrrole administered to mice or rats at doses approaching the LD$_{50}$ produced retardation of spontaneous movement, muscle weakness and flaccidity, and ascending hind-limb weakness with the animals eventually lying immobile on their sides or backs. There was abdominal relaxation, and depression of flexion withdrawal and of the pineal reflex. The righting reflex was depressed and then lost. The animals remained able to hang and to support their weight on an inclined screen, when partially immobilized and made flaccid by the drug. Slowing of respiration occurred but there was no evidence of impaired ventilation until terminally. Drug effects were evident within 10 minutes after oral administration in mice. Death generally occurred at 15 to 20 minutes with the oral dose, and at 10 to 15 minutes after intraperitoneal injection. Terminally, mice turned over on their backs and clonic spasms occurred in the hind limbs. Intravenous administration in rats produces instantaneous death in a minority of trials; more frequently there was generalized slowing and flaccidity by 10 to 15 minutes followed by hind-limb paralysis, and death, resulting from respiratory arrest, usually occurring within one hour but delayed for 2 and 3 hours in some specimens. Surviving animals appeared normal by 4 to 5 hours after administration of the drug.

There was no change observed in behavior or on physical examination of the mice or rats at doses of 15 mgm. per kg. orally or parenterally. With doses above 50 mgm. per kg. there was a progressive slowing of spontaneous activity and paresis of the hind limbs.

Ten and 15 mgm. per kg. injected intraperitoneally into healthy adult cats caused no change in behavior; 100 mgm. per kg. produced ataxia and apparent muscle weakness. It is noteworthy that no change in behavior was apparent in the intact cat at a dose of 5 to 10 times that demonstrated to depress spinal reflex excitability recovery and diminish spasticity and the flexion reflex in the animal preparation.

EXAMPLE 4

It has been possible to analyze the pharmacological activity and specificity of effect of standard "muscle relaxants" and to establish physiological criteria for a centrally acting skeletal muscle relaxant. Depression of monosynaptic reflex recovery (technique of paired stimuli) is a particularly sensitive index of clinical effectiveness. Changes in recovery and excitability of the monosynaptic and flexion reflexes are supplemented by evidence derived from classical animal testing procedures.

The apparatus for immobilizing the animal and for delivering a regular blow to the Achilles tendon has been described (Gassel, M. M. and Pompeiano, O., Arch. Ital. Biol., 103:347-368, L (1965). The technique for stimulating the post tibial nerve and for eliciting the electrically evoked monosynaptic reflex and studying the recovery curve of the reflex (technique of paired stimuli) from the same population of triceps surae motoneurones has been reported (Gassel, M. M., J. Neurol. Neurosurg. Psychiat., 33:358-362, (1970). Stretch reflexes have also been studied by slow stretch of the triceps surae muscle (Ginzel, K. H. et al, Neuropharmacology, 9:369-379, (1970). The flexion reflex is studied by delivering an invariable shock through electrodes fixed in place subcutaneously on the plantar surface of the foot and recording electromyographic activity associated with reflex withdrawal from electrodes implanted in the tibialis anterior. The techniques of stimulating and recording are designed for maintaining stability of conditions over long periods. Intrarterial blood pressure, pulse, and respiration are recorded on a polygraph simultaneous with reflex studies. The reflex is monitored independently on a storage oscilloscope. Cats lightly anesthesized with chlorulose-urethane or intra-peritoneal nembutal, and unanesthesized decerebrate preparations (mid-collicular) are studied.

1-methyl and 1,5-dimethyl-2-(3-pyridyl) pyrrole and the hydrochloride salts of these compounds depress excitability and recovery of the monosynaptic reflex. The earliest effect and the most profound inhibition is on reflex recovery. Electrically and mechanically evoked monosynaptic reflexes are affected to an equal degree. The reflex is depressed 5% to 10% with an intravenous dose of 0.5 to 1 mgm. per kg., and the depression progresses up to 30 to 40% at 3 to 4 mgm. per kg. Residual muscle activity recorded electromyographically, is depressed by the drug. There is decrease in the ipsilateral flexion reflex and crossed extension evoked by a regular shock to the skin, at a dose of 2 mgm. per kg. Decrease in rigidity of the mid-collicular decerebrate preparation occurs at 2 to 3 mgm. per kg., and spasticity is diminished and the crossed extension reflex reduced in 5 of 6 chronic preparations with lesions of either cerebral or spinal origin. Slight depression of the blood pressure (about 5 mm. of Hg.) and transient slowing of respiration sometimes occurs with doses below 2 mgm. per kg. There is sometimes a transient increase in blood pressure of 5 to 15 mm. of Hg. and slight slowing of pulse and respiration at 2.5 to 5 mgm. per kg.

Reflex depression is generally apparent within 1 minute of the injection, peak effect is at 3 minutes to 20 minutes, and the drug action remains evident for over one hour with larger doses.

1,5-dimethyl-2-(3-pyridyl) pyrrole produces a similar pattern of change in reflex recovery and excitability at the same dose levels. The onset of effect is delayed for 3 to 5 minutes after the intravenous injection and the duration of effect is longer than with 1-methyl-2-(3-pyridyl) pyrrole.

There is no change in the direct motor response evoked in the triceps surae on supramaximal stimulation of the posterior tibial nerve (3 c/s for 5 seconds) at a dose of 100 mgm. to 200 mgm. per kg. This indicates an absence of peripheral neuromuscular block at high dose levels.

The muscle relaxant effects of pentobarbital sodium, diazepam and orphenadrine citrate have been investigated in the same animal preparations. Diazepam at an intravenous dose of 100-250 gm. per kg. in cats and pentobarbital sodium at 1.0 to 2.0 mgm. per kg. produces depression of blood pressure of 25 to 35 mm. of Hg., slowing of respiration and pulse rate and a fall in reflex amplitude of 10 to 30 percent. Depression of the flexion reflex first occurs at 150-200 gm. per kg. of diazepam and 1,5 to 2.0 mgm. per kg. of pentobarbital sodium. Orphenadrine at an intravenous dose of 1.2 mgm. per kg. produces a preliminary drop in blood pressure of 35 mm. of Hg. followed by a 35 mm. rise above control before returning to normal. Fluctuations in monosynaptic reflex amplitudes are presumed to be associated with the occurrence of spontaneous muscle activity after the drug. At higher doses the animals appear alerted and the swing in blood pressure increases in extent.

The inhibitory effect of 1-methyl-and 1,5-dimethyl-2-(3-pyrridyl) pyrrole on spinal monosynaptic reflexes is additional to that of barbiturate induced reflex depression. It is therefore preferable to employ the drug with "sedative" muscle relaxants such as diazepam and barbiturates to enhance central reflex inhibition.

The neurophysiological criteria for activity as a central muscle relaxant are satisfied. There are: 1) depression of recovery and excitability of the spinal monosynaptic reflex, 2) inhibition of the flexion reflex 3) decrease in spasticity and rigidity in the animal preparation 4) minimal changes in blood pressure, pulse, and respiration at pharmacologically active doses.

The subject matter which the applicant regards as his invention is particularly pointed out and distinctly claimed as follows:

I claim:

1. A method for inducing skeletal muscle relaxation in a mammal suffering from a pathological state characterized by hyperactivity of the spinal reflex arc, which comprises the administration to said mammal of a pharmaceutically effective non-toxic amount of 1-methyl-2-(3-pyridyl) pyrrole.

2. A method according to claim 1 wherein the route of administration is oral.

3. A method according to claim 1 wherein the route of administration is parenteral.

4. A method for inducing skeletal muscle relaxation in a mammal suffering from a pathological state characterized by hyperactivity of the spinal reflex arc, which comprises the administration to said mammal of a pharmaceutically effective non-toxic amount of 1,5-dimethyl-2-(3-pyridyl) pyrrole.

5. A method according to claim 4 wherin the route of administration is oral.

6. A method according to claim 4 wherein the route of administration is parenteral.